(12) United States Patent
Paull et al.

(10) Patent No.: US 11,801,406 B2
(45) Date of Patent: Oct. 31, 2023

(54) SPECIAL FIRE PROTECTION SYSTEM FOR RUNAWAY GRASS AND FOREST FIRES AND METHOD FOR USE

(71) Applicants: Lee D Paull, Carmel, IN (US); Marcus S Ramsey, Noblesville, IN (US)

(72) Inventors: Lee D Paull, Carmel, IN (US); Marcus S Ramsey, Noblesville, IN (US)

( * ) Notice: Subject to any disclaimer, the term of this patent is extended or adjusted under 35 U.S.C. 154(b) by 0 days.

(21) Appl. No.: 16/679,232

(22) Filed: Nov. 10, 2019

(65) Prior Publication Data

US 2020/0147423 A1 May 14, 2020

Related U.S. Application Data

(60) Provisional application No. 62/767,178, filed on Nov. 14, 2018.

(51) Int. Cl.
| | |
|---|---|
| *A62C 3/02* | (2006.01) |
| *C12N 1/20* | (2006.01) |
| *C12N 9/22* | (2006.01) |
| *C12N 15/11* | (2006.01) |
| *C12N 15/74* | (2006.01) |
| *C12N 15/86* | (2006.01) |

(52) U.S. Cl.
CPC .......... *A62C 3/0214* (2013.01); *A62C 3/0257* (2013.01); *C12N 1/205* (2021.05); *C12N 9/22* (2013.01); *C12N 15/111* (2013.01); *C12N 15/74* (2013.01); *C12N 15/86* (2013.01); *C12N 2310/20* (2017.05)

(58) Field of Classification Search
CPC ....... A62C 3/0214; A62C 3/0257; A62C 5/02; A62C 99/0036; E04B 1/94

USPC ........................................................... 169/45
See application file for complete search history.

(56) References Cited

U.S. PATENT DOCUMENTS

| | | | | |
|---|---|---|---|---|
| 2,455,237 | A * | 11/1948 | Davis .................... | B60P 7/0876 |
| | | | | 410/97 |
| 3,659,641 | A * | 5/1972 | Marino .............. | B65D 71/0096 |
| | | | | 206/597 |
| 3,715,843 | A | 2/1973 | Ballinger | |
| 4,597,450 | A * | 7/1986 | Budmiger ................ | A62C 8/06 |
| | | | | 383/207 |
| 4,858,395 | A | 8/1989 | Mcquirk | |

(Continued)

FOREIGN PATENT DOCUMENTS

WO        WO-9744094 A1 * 11/1997         ........... A62C 3/0257

*Primary Examiner* — Tuongminh N Pham
*Assistant Examiner* — Kevin Edward Schwartz
(74) *Attorney, Agent, or Firm* — Ritchison Law Offices, PC; John D Ritchison

(57) ABSTRACT

A Fire Protection System for Runaway Grass and Forest Fires and Method for Use for protecting residential, commercial and governmental structures made of a heat reflective cover configured to fully encase the structure, a fire proof spray foam—approximately 2 to 12 inches, with fire retardant additive, multiple hold down straps, a series of anchors, a pre spray release coating a set of corner bands whereby the system, broadly considered, can be individually installed into a position to completely isolate a free standing structure from an external fire and can be readily customized to fit varying size structures which can prevent damage to a free standing structure and its contents from an external wild fire or firestorm.

9 Claims, 12 Drawing Sheets

(56) References Cited

U.S. PATENT DOCUMENTS

| | | | |
|---|---|---|---|
| 4,956,218 A * | 9/1990 | Haining | A62C 8/06 428/920 |
| 4,994,317 A | 2/1991 | Dugan et al. | |
| 5,047,449 A | 9/1991 | Pastureau | |
| 5,423,150 A | 6/1995 | Hitchcock | |
| 5,608,992 A | 3/1997 | Floyd | |
| 5,860,251 A | 1/1999 | Gleich | |
| 5,931,233 A | 8/1999 | La Bonte et al. | |
| 5,968,669 A | 10/1999 | Liu et al. | |
| 6,113,031 A * | 9/2000 | Williams | B64D 9/00 220/1.5 |
| 6,810,626 B2 | 11/2004 | Meyer et al. | |
| 7,395,869 B2 | 7/2008 | Schnabel et al. | |
| 8,006,447 B2 * | 8/2011 | Beele | A62C 2/065 52/232 |
| 8,127,387 B2 * | 3/2012 | Tygh | A62B 3/005 7/166 |
| 9,381,387 B2 | 7/2016 | Douglas | |
| 9,956,445 B2 * | 5/2018 | Enk, Sr. | B05B 12/087 |
| 2005/0022466 A1 | 2/2005 | Kish et al. | |
| 2005/0170725 A1 | 8/2005 | Kimener | |
| 2009/0301001 A1 | 12/2009 | Kish et al. | |
| 2010/0025054 A1 * | 2/2010 | Jesclard | A62C 3/065 29/428 |
| 2010/0269449 A1 | 10/2010 | Bush et al. | |
| 2012/0227990 A1 | 9/2012 | Burnham | |
| 2013/0048317 A1 | 2/2013 | Charlton | |
| 2013/0118764 A1 * | 5/2013 | Porter | H02G 3/22 169/48 |
| 2014/0202721 A1 * | 7/2014 | Shaw | A62C 3/14 169/48 |
| 2015/0083443 A1 | 3/2015 | Thompson | |
| 2016/0047120 A1 | 2/2016 | Davis et al. | |
| 2017/0021208 A1 * | 1/2017 | Dor-El | A62C 3/0257 |
| 2017/0274232 A1 * | 9/2017 | Kreuser | A62C 3/0214 |
| 2020/0316421 A1 * | 10/2020 | Patzelt | A62C 3/0214 |
| 2022/0001222 A1 * | 1/2022 | Dor | B64D 1/16 |

\* cited by examiner

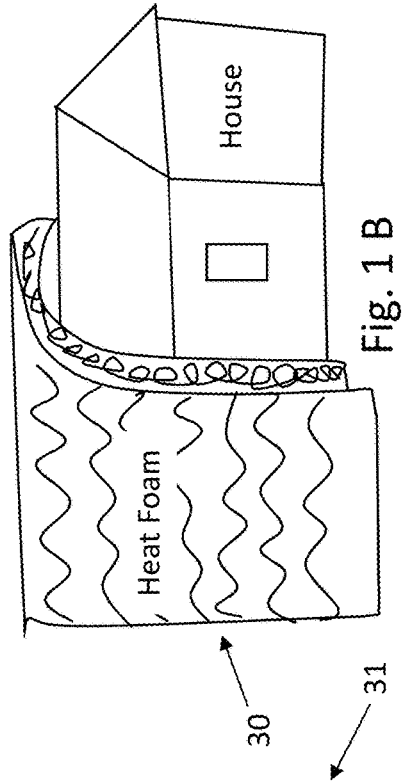
Fig. 1B
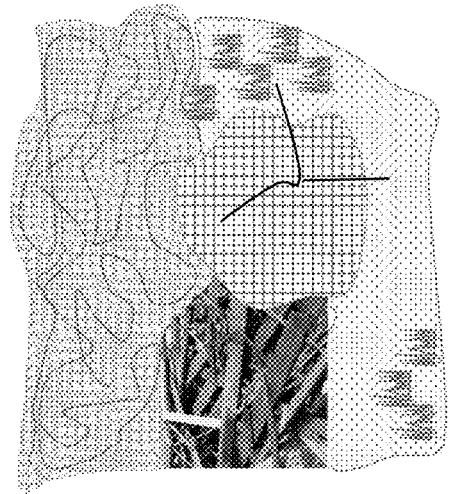
Fig. 1A
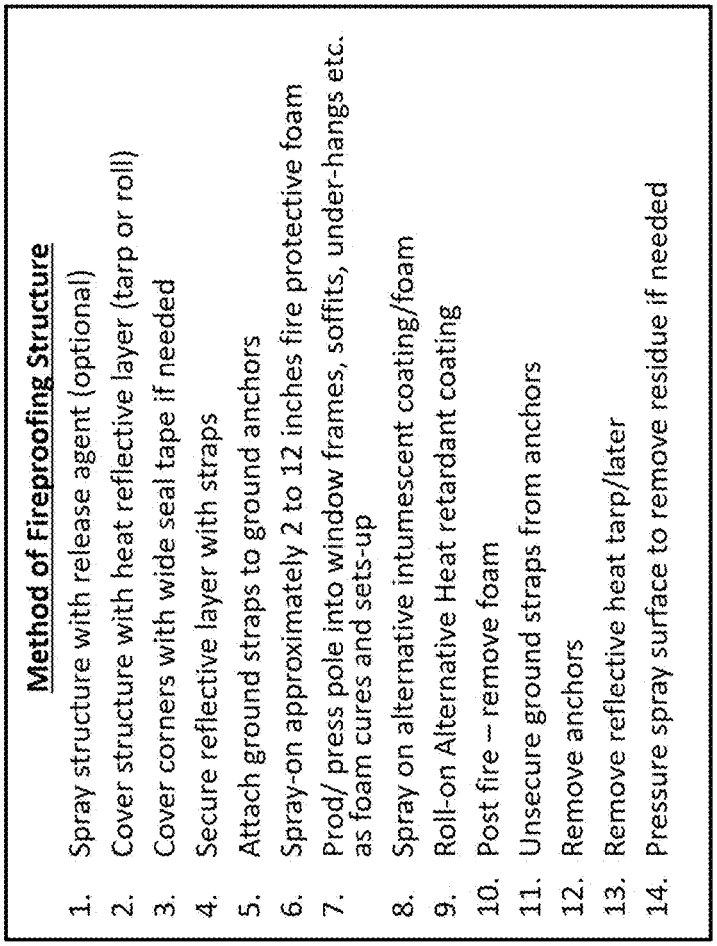
Fig. 1D
Fig. 1C

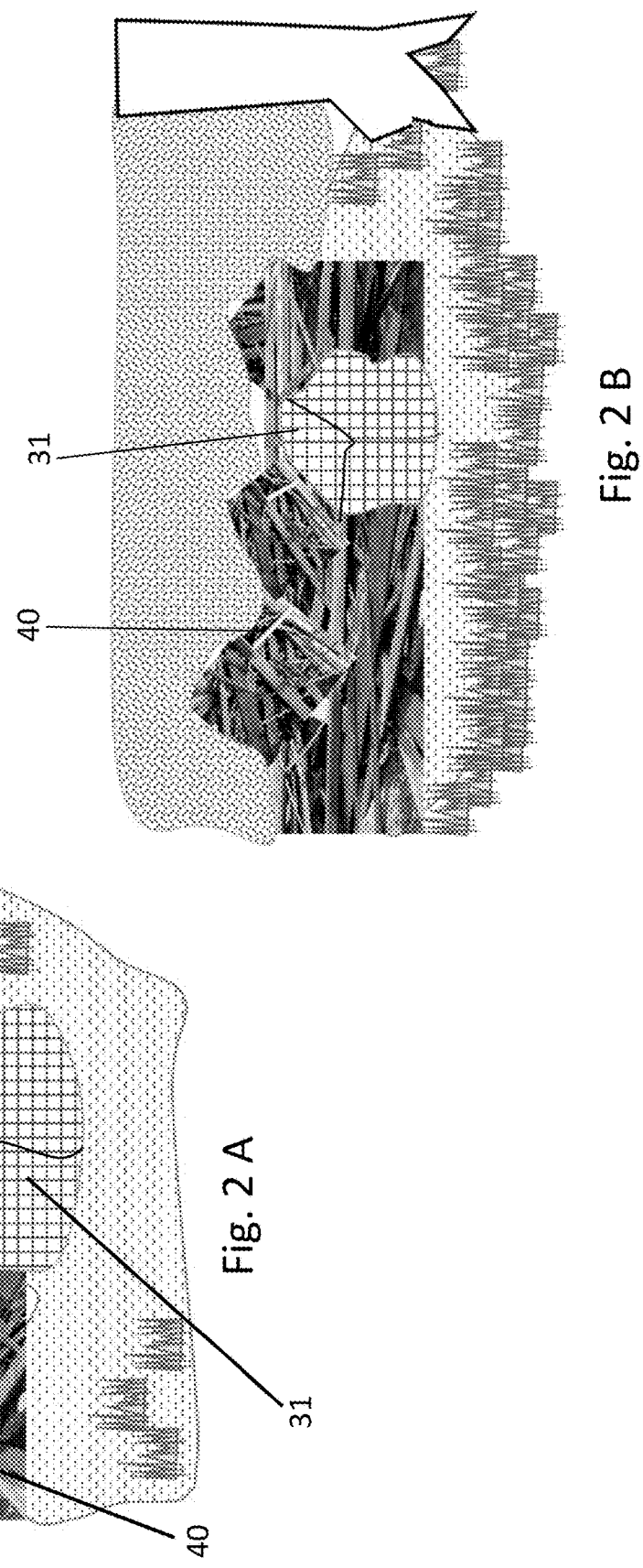

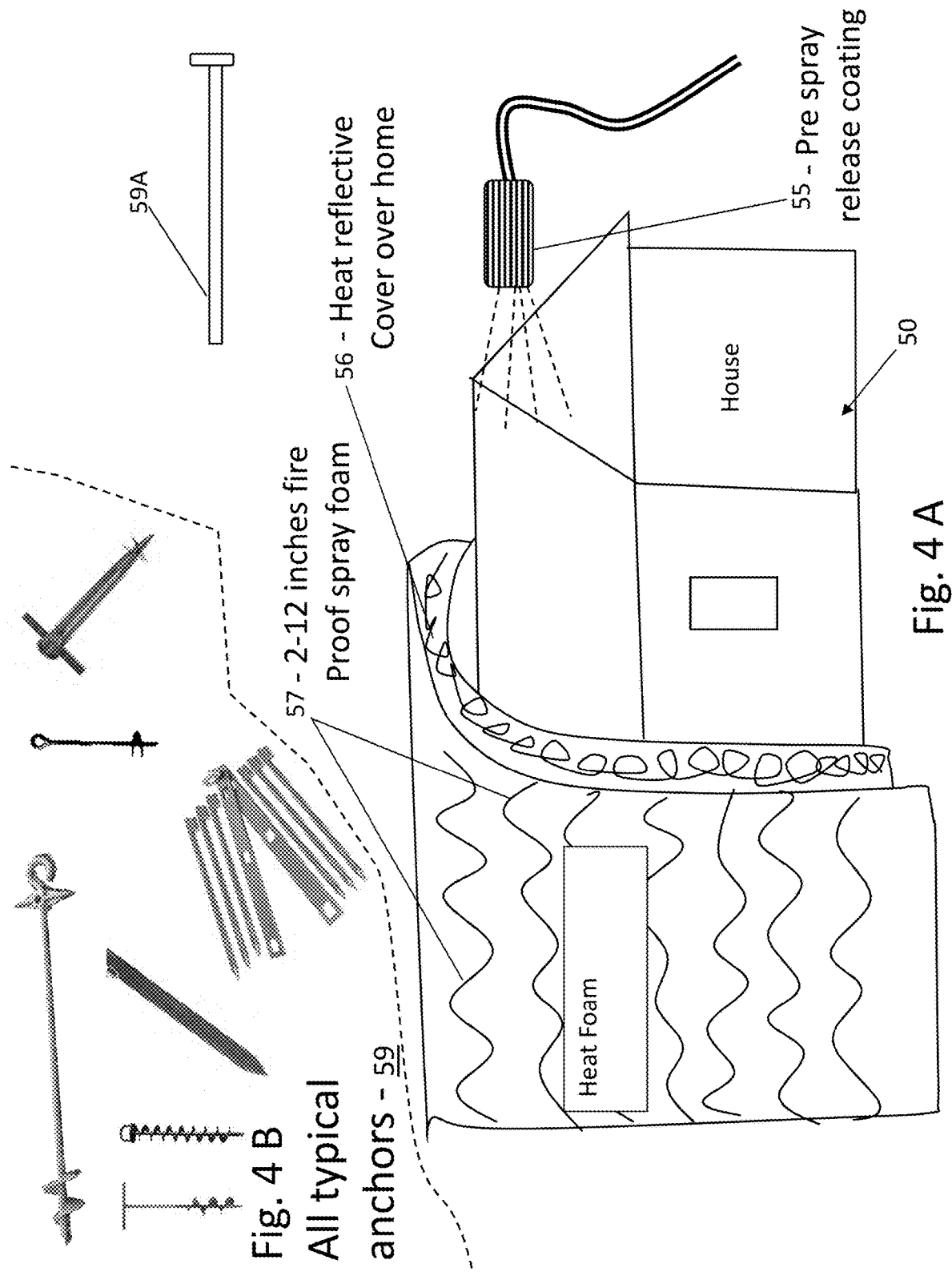

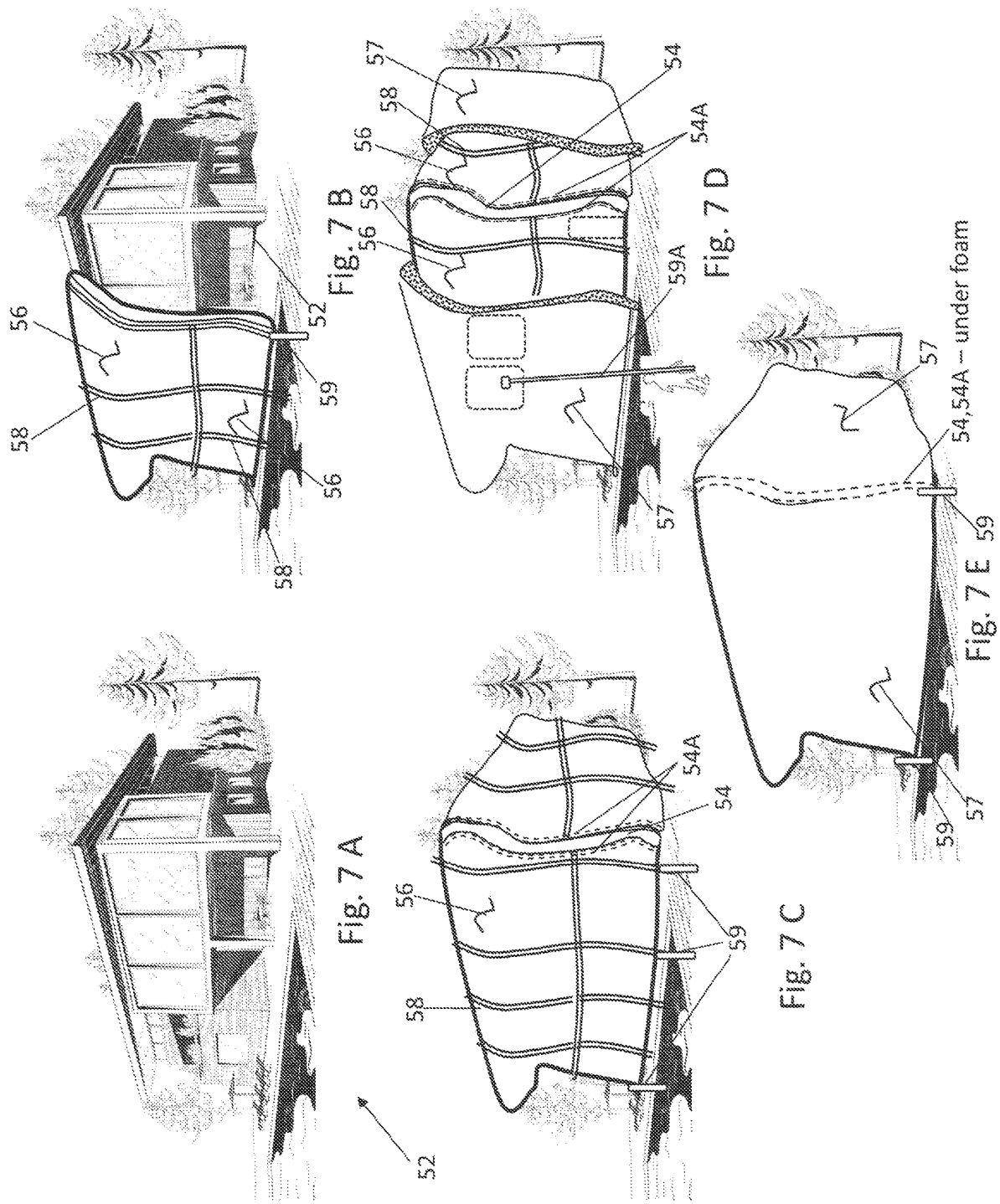

Method of Fireproofing Structure

1. Spray structure with release agent (optional)
2. Cover structure with heat reflective layer (tarp or roll)
3. Cover corners with wide seal tape if needed
4. Secure reflective layer with straps
5. Attach ground straps to ground anchors
6. Spray-on approximately 2 to 12 inches fire protective foam
7. Prod/ press pole into window frames, soffits, under-hangs etc. as foam cures and sets-up
8. Spray on alternative intumescent coating/foam
9. Roll-on Alternative Heat retardant coating
10. Post fire – remove foam
11. Unsecure ground straps from anchors
12. Remove anchors
13. Remove reflective heat tarp/later
14. Pressure spray surface to remove residue if needed

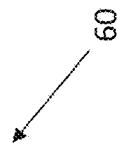

Fig. 8

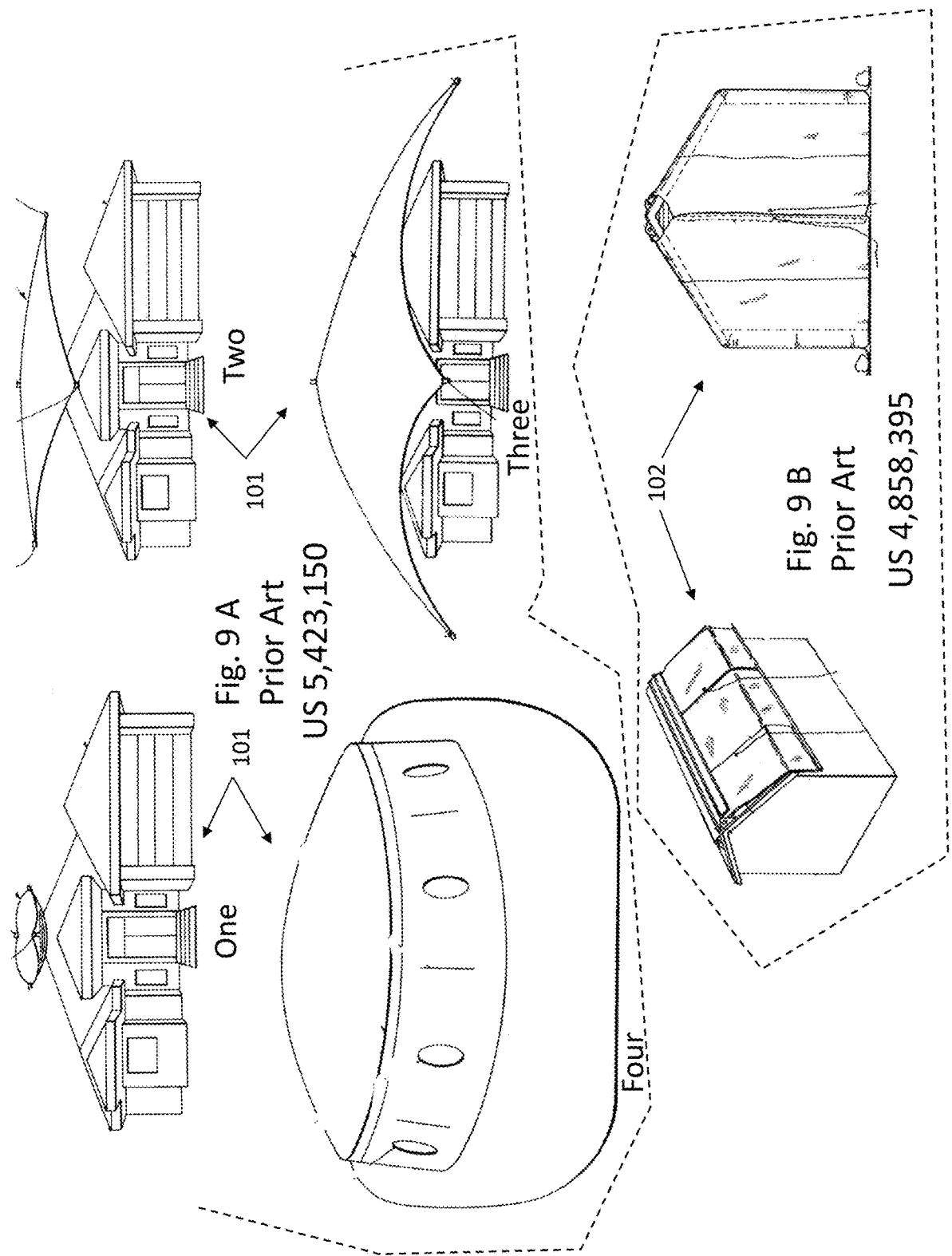

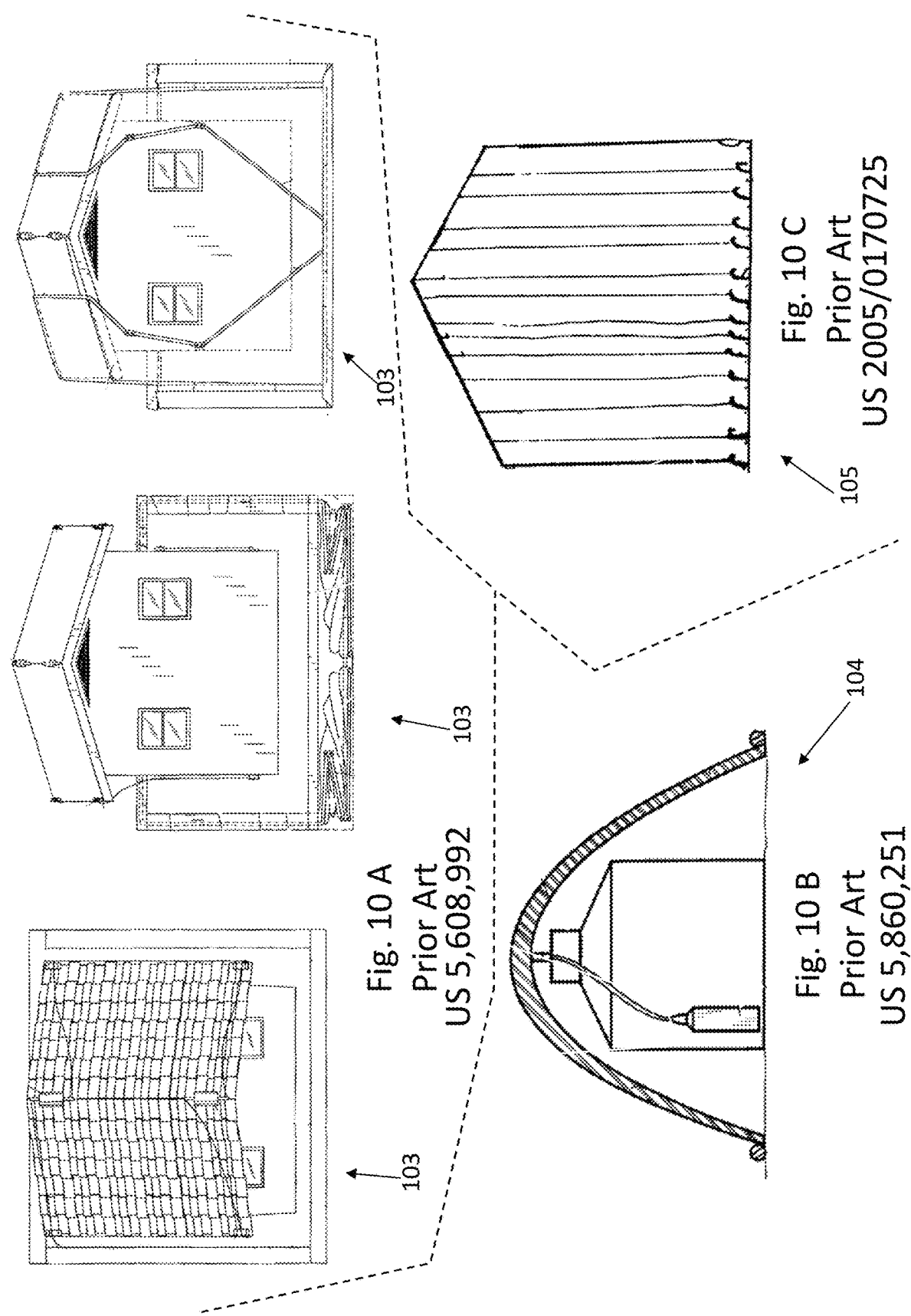

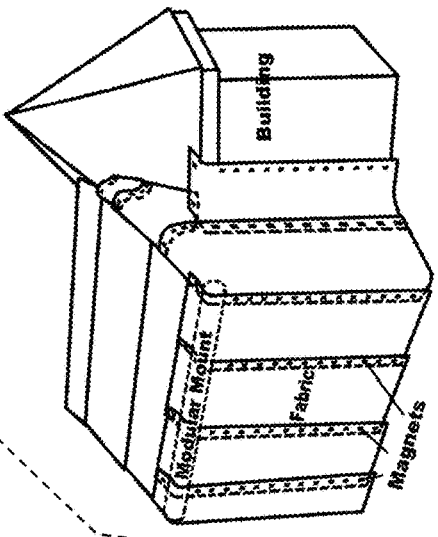
Fig. 11B Prior Art
US 7,395,869
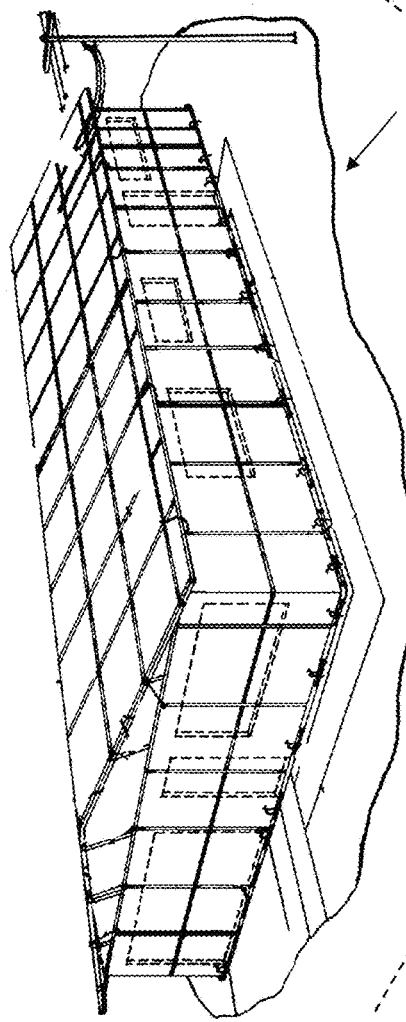
Fig. 11A US 3,715,843 Prior Art
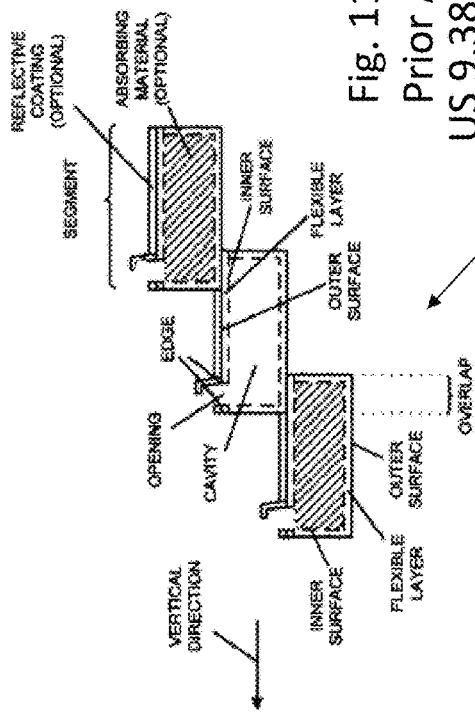
Fig. 11C Prior Art
US 9,381,387

US 2010/0269449

US 2012/0227990

SPECIAL FIRE PROTECTION SYSTEM FOR RUNAWAY GRASS AND FOREST FIRES AND METHOD FOR USE

CROSS-REFERENCE TO RELATED APPLICATIONS

This application claims the benefit of United States Provisional Patent Application with Ser. No. 62/767,178 filed Nov. 14, 2018, by Lee D. Paull. The provisional application is entitled "Special Fire Protection System for Runaway Grass and Forest Fires and Method for Use".

FIELD OF INVENTION

This invention relates to a Special Fire Protection System for Runaway Grass and Forest Fires and Method for Use. Simply stated it is related to fire protection systems for structures. The embodiments herein are particularly related to fire protection devices and accessories used for protecting building structures. The embodiments herein are more particularly related to fire protection sheet and insulating blanket of foam used for protecting building structures without direct physical attachments to the building structure. More particularly, the present invention relates to a design for fire-resistant structure deployed over buildings and other objects when confronted with an approaching fire.

Furthermore, the present disclosure relates to system and method of use for a system that protect objects from damage or combustion when exposed to fire. This is a design of a system for emergency deployment in the event of the approach of hazardous conditions, especially rapidly moving fires commonly referred to as "fire storms." The present invention relates generally to a fire isolation covering system for free standing structures. More particularly, the present invention relates to a system for a fire resistant house cover which can be employed as well for other structures, residential and commercial.

FEDERALLY SPONSORED RESEARCH

None.

SEQUENCE LISTING OR PROGRAM

None.

BACKGROUND-FIELD OF INVENTION AND PRIOR ART

As far as known, there are no Special Fire Protection System for Runaway Grass and Forest Fires and Method for Use. It is believed that this protection system and method of use are unique in their design and technologies.

BACKGROUND

This is background as to a Special Fire Protection System for Runaway Grass and Forest Fires and Method for Use. It is well known that a basic concern in protecting a building structure from an approaching fire is the ability to quickly and effectively deploy a fire resistant material or blanket around the entire structure before a fire starts. Often there is little warning of an approaching fire, particularly if the threatening fire spreads at night or while an occupant is away from his home. Even if a homeowner is present, the rapid movement of fire storms driven by high winds can still result in extensive property damage before conventional precautionary measures can be taken. Without the ability to quickly, completely, and automatically deploy a fire protection system, the building structure may quickly succumb to the approaching fire. It is deemed desirable to develop a fire protection system that does not expose a person or persons to the dangers of an approaching fire. Thus, the ability to quickly deploy the fire protecting system is a primary goal inadequately addressed by the prior art.

Fires, particularly fierce brush fires, bush fires and wildfires that affect large acreages and results in destruction of households, businesses, buildings, industrial plants or other structures, as well as forests, pastures or parks are all too common. They result in great personal tragedies, natural disasters as well as in immense economic losses. These fires may be caused by or connected with lightning, storms, firestorms, earthquakes, hurricanes, tornadoes, natural causes, human negligence or arson. Many of these fires spread quickly and become uncontrollable. Wildfires burn an average of 5 million acres of prairie and woodlands every year in the U.S. alone. Some fires start naturally and some are the result of arson or of carelessness by hikers or campers. Once a wildfire starts, it can advance at a velocity of about 6.8 mph in forests and up to 14 mph in grasslands. Additionally, the wind can carry embers far ahead of the fire line and start new fires elsewhere. The rate of spread depends on the availability of dry grass or wood, topography, wind speed, ambient temperature and humidity. Direction of spread of fire can be influenced not only by the distribution of fuel but by the wind. Accordingly, some fires change direction abruptly and threaten structures with little warning.

Every year free standing structures are either destroyed or endangered by out of control forest fires. These forest fires burn out of control usually because they are just too large for firefighting personnel to contain. Out of control forest fires can easily destroy any free standing fire prone structure in their path. Therefore, there is a need for a fire protection device that can isolate free standing fire prone structures such as single family homes from out of control forest fires. It is well known that certain geographical areas, particularly California, are prone to wildfires which can rage through inhabited areas destroying residential and commercial property worth millions of dollars. Wildfires are often ignited by natural phenomena such as by lightning storms or caused by mankind. Once a wildfire is ignited, it creates an environment that requires fuel, oxygen, and suitable temperature conditions to continue to exist. Also, an area which has remained without burning for some years will have accumulated a great amount of fuel and will likely have fires of greater intensity. If the fuel load in a forest is high, the fire can burn with great intensity and reach the canopy of the forest and burn the trees in their entirety. It can also result in a crown fire which will burn the tops of the trees and other aerial fuels and spread at a different rate from the surface fire. A smaller surface fuel load with no significant presence of ladder fuels may result in a fire that only clears up the brush and leaves the canopy intact, allowing trees to survive and seeds to eventually sprout and regenerate vegetation on the forest floor.

Temperatures of these fires can, at certain points, reach 1400 degrees C. and may easily reach temperatures over degrees C. Moreover, such fires may be caused or accompanied by winds, or wind gusts reaching up to 150 miles/hour. Whatever their origin, these fires are extremely dangerous and very hard to bring under control. Additionally, some of the fires, for example, bush or forest fires may advance at a rate of from 0.5 km/hour to more than 6 km/hour. The speed and intensity of these fires depends on the type of terrain and on weather conditions. The flames of these fires may reach the height up to 50 meters. These kinds of fires often exceed temperatures above 1600 degrees C. and, under extreme conditions, can give off 10,000 kilowatts per meter of fire front (Canadian Forest Service Report at www.nofc.forestry.ca/fire). Additionally, many of the fires end up becoming firestorms.

In fact, firestorms are conflagrations which attain such intensity that they create and sustain their own wind system. This phenomenon is particularly often observed in bush fires, brush fires, forest fires and wildfires. The firestorms are created as a result of the stack effect occurring when the heat of the original fire draws in more and more of surrounding air, thereby creating turbulence and erratic changes in wind direction. The wind shear generated during firestorms is capable of producing small tornado-like fire whirls that may result in a quick spread of fire not only to adjacent but also to more remote areas. Moreover, the draft generated during firestorms may draw in large quantities of oxygen thereby significantly increasing heat and combustion.

Clearly, the uncontrollable fires and firestorms create very dangerous and economically unsustainable conditions and problems and there is a continuing need to provide solutions to these problems. Although throughout the years attempts were made to provide solutions to these problems, so far there is no reliable, practical and economical way to protect houses, businesses and other structures and objects from these uncontrollable fires and firestorms. It would therefore be advantageous to provide means for protecting housing and other structures and objects from fires and firestorms having extremely high temperatures and also those that are accompanied by winds or other extreme conditions that further prevent these fires to be controlled and extinguished.

In the presence of a well-developed fire (such as a wild fire in a remote area or a building fire in an urban area), structures often join the main conflagration from ignition because of one or more factors. For example, ignition of the structures may be caused by: sparks and burning cinders being blown onto them, by spontaneous ignition due to their being superheated to an ignition point (such as due to absorption of infrared radiation), and/or by engulfment by the main fire. The primary technique for preventing ignition of structures in the case of wild fires is prevention. For example, local ordinances often require the clearing of brush, weeds, trees, free wood and other combustibles in areas around structures in rural or fire-prone areas.

Once a wild fire is established, evacuations are generally ordered for areas in the path of the fire, and fire prevention and suppression is turned over to trained firefighting crews. In the case of wild fires, the firefighting crews often use dropped fire retardants, aerial water drops, fire lines and other techniques to extinguish fires. As a wild fire approaches structures, the firefighting crews create fire lines (i.e., areas that are devoid of combustible materials) to keep the encroaching fires at a distance in an attempt to prevent secondary ignition. When water or fire-retardant chemicals are available, the fire fighting fire crews will also treat the structures (and the surrounding areas) with the water or the fire-retardant chemicals to prevent secondary ignition. One of the last defensive techniques is to directly apply water to the structures so that, if secondary ignition occurs because of sparks or rising temperatures, the fire is suppressed at the time of ignition. However, in the event of restrictions on resources or a low probability of successful fire control, structures may be abandoned to the flames. In each of these scenarios, preventing secondary ignition of structures involves the commitment of resources, in terms of manpower and water. Because these resources are often limited, these firefighting efforts represent a major drain on resources and can complicate firefighting efforts. In addition, in the event that the firefighting efforts are unsuccessful, there is a considerable burden in terms of lost property, financial and emotional damage, and loss of life.

In order to protect building structures, including homes, from these uncontrolled external fires, there have been numerous attempts to develop fire protection devices which can isolate the building structures from these external fires. In particular, various systems and methods for enclosing the building structures from surrounding external fires by placing fire resistant materials over building structures have been proposed and utilized. However, the prior art devices and methods generally involve impractical, complicated deployment mechanisms and/or require external power sources for deployment which are often unavailable. Prior approaches to deployable fire protection devices depended primarily on unfurling curtains or thin sheets made of fire-retardant material to protect buildings from "sparks and flame." Such devices have several important drawbacks. Notably they are difficult and time-consuming to deploy and provide little or no temperature reduction to the structure being protected. Temperatures in a fire-storm can reach in excess of the ignition point for wood and other combustibles. Therefore, maximizing the thermal barrier at the structure is essential. The time and effort required to deploy a fire-protection device is critical since in the face of an approaching firestorm, evacuation of people necessarily takes precedence over the protection of structures. The easier and faster the deployment, the higher the likelihood that the apparatus will be successfully used. Additionally, the faster such a device is set-up, the quicker people can be evacuated, thereby increasing the safety margin. Therefore the present invention represents a significant improvement over prior art.

Problem Solved

The improvement and problem solved as to fire protection systems naturally evolve from the background of the overall condition of wildfires described above. Every year free standing structures are either destroyed or endangered by out of control forest fires. These forest fires burn out of control usually because they are just too large for firefighting personnel to contain. Out of control forest fires can easily destroy any free standing fire prone structure in their path. Therefore, there is a need for a fire protection device that can isolate free standing fire prone structures such as single family homes from out of control forest fires.

There are also needs as follows: provide a fire protection device with a simple and reliable deployment system that does not rely on any external power source; provide a fast and effective method of quickly enveloping a building structure from an external fire; and provide a barrier system for protection and resistance from externally started fires, forest fires and other fires that effect and start a structure burning from the outside inward. Hence, there is a need for improved an improved technique for protecting structures (and, more generally, objects) from fire. Numerous innovations for fire isolation devices have been provided in the prior art that are described as follows. Even though these innovations may be suitable for the specific individual purposes to which they address, they differ from the present invention as hereinafter contrasted.

As far as known and believed, there are no Special Fire Protection Systems for Runaway Grass and Forest Fires and Method for Use. It is believed that this system is unique in its design and technologies. A novelty search revealed:

A. U.S. Pat. No. 3,715,843 by Ballinger was issued in 1973 for a PROTECTION APPARATUS FOR A BUILDING. It teaches a fire-resistant apparatus for covering and enclosing a building for protecting it from airborne firebrands, or the like, produced by a high-velocity fire storm. The enclosing apparatus includes flexible, thin-sheet cover means of fire-resistant or fire-retardant material which is usually in the form of several panel portions and a protective fire-retardant cover interposed between the panels that is easily assembled and mounted in protective relationship over a building by a small crew of men when the building is threatened by an approaching fire storm. Next, B. a U.S. Pat. No. 4,858,395 by McQuirk was issued in for a FIRE PROTECTION FOR STRUCTURES. It demonstrated a fire protection device for a structure using a fire resistant sheet material compacted in a folded condition in a housing on the roof of the structure so that when deployed from the housing it can be unfolded to quickly envelop the structure. After that, C. a U.S. Pat. No. 4,994,317 by Dugan et al. was issued in 1991 for a FLAME DURABLE FIRE BARRIER FABRIC. This provides a fabric suitable for use as a flame barrier fabric comprising a flame durable textile fabric substrate, a flexible silicone polymer layer which stays intact, maintains its integrity on exposure to a flame and is carried by the surface of the textile fabric substrate, and a reflective flame durable paint coating carried by the silicone polymer coating. Next, D. a U.S. Pat. No. 5,047,449 by Pastureau was issued in 1991 for a FIRE PROTECTION MATERIAL. Here is shown a material characterized in that it is flexible, employs simultaneously the two phenomena of in tumescence and endothermicity to obtain optimal protection characteristics maintaining the element to be protected at a temperature below or in the order of 150 degrees C. when it is subjected to thermal attack corresponding to a flame temperature of 700 to 1000 degrees for a duration of at least one hour and for a thickness of the material between 10 and 20 millimeters.

E. A U.S. Pat. No. 5,423,150 by Hitchcock was issued in 1995 for an AUTOMATED EXTERIOR FIRE PROTECTION SYSTEM FOR BUILDING STRUCTURES. It exemplifies an automated exterior fire protection system deploys a fire resistant blanket that is stored under the roof of the structure. Threatening fires are detected by a sensor to provide a signal that initiates automatic deployment of the blanket. F. Next a U.S. Pat. No. 5,608,992 by Floyd was issued in 1997 for a FIRE RESISTANT HOUSE COVER. It is a fire isolation device for a free standing structure. This device includes a left tarp and right tarp fabricated from a fire resistant material. The left tarp and right tarp are of a size to completely enclose the free standing structure. Then, G. a U.S. Pat. No. 5,860,251 by Gleich was issued in 1999 for a RAPIDLY DEPLOYABLE FIRE-PROTECTION APPARATUS. It profiles a fire-resistant flexible dome apparatus for covering and protecting buildings, goods, livestock, persons and other objects from a fire, especially a rapidly moving conflagration known as a "fire storm." The apparatus is a dome-like structure made of fire-retardant fabric, supported with air or gas pressure within integral tubes radially disposed about the central axis, or between one or more layers of said fire resistant fabric. Its ground-contacting periphery is manually secured to the ground. One embodiment is provided to add an improved ground seal and added anchoring to ground to help maintain structural integrity. Air or gas pressure may be provided by several means including compressed gas, mechanical air movement or chemical devolution. Then, H. a U.S. Pat. No. 5,931,233 by La Bonte, et al. was issued in 1999 for a TWO-PHASE FIRE SUPPRESSION/PROTECTION METHOD AND SYSTEM FOR STRUCTURES AND SURROUNDING GROUNDS. It is a two-phase fire suppression/protection method and system for structures and surrounding grounds includes a Phase1 and a Phase2. Phase1 is initiated first when a plurality of parabolic microphone sensors placed at the perimeter of the grounds surrounding the structure detect sound associated with an advancing wildfire. The distribution units generate a dome of high pressure cool air which encapsulates the structures and surrounding grounds for impeding the approach of the wildfire. Phase1 also employs a set of fog jet nozzles which atomize water under high pressure to produce a cool fog dispersion pattern which provides complete wide-area wetting and is sufficient to create, by air displacement, a high pressure envelope surrounding the structure. Phase2 is initiated as the approaching flames are detected by additional sensors including smoke/particulate, thermal, and infrared sensors. Phase2 employs a set of spiral jet nozzles which are intended to create a dispersion that deluges the entire surface area of the structure with water.

I. A U.S. Pat. No. 5,968,669 by Liu et al. was issued in 1999 for a FIRE RETARDANT INTUMESCENT COATING FOR LIGNOCELLULOSIC MATERIALS. It provides a fire retardant coating composition for lignocellulosic materials which comprises expandable graphite particles, an absorbent material, a polymeric binder, a carbonific material, a blowing agent, and a wetting agent. Next J. a U.S. Pat. No. 6,810,626 by Meyer et al was issued in 2004 for a FIRE PROTECTION DEVICE FOR A BUILDING STRUCTURE. It shows and teaches fire protection devices and related methods for isolating building structures from an external fire. The fire protection device includes a rolled fire-resistant protective cover having dimensions large enough to cover the building structure. The protective cover is then stored in a storage bag storing the protective cover and being disposed on an inclined top surface of the building structure. The device includes means for releasing the rolled protective cover from the storage bag so that, upon release from the storage bag, the protective cover can roll down the inclined top surface by gravity. K. A U.S. Pat. No. 7,395,869 by Schnabel, et al. was issued in 2008 for an EXTERNAL STRUCTURE FIRE PROTECTION SYSTEM—"ESFPS". It demonstrates a barrier system for protection and resistance from externally started fires, forest fires and other fires that effect and start a structure burning from the outside inward. The barrier system comprising a specifically designed track system mounted onto the top of the structure, utilizing fire protective material hanging down the sides of the structure to create a fire resistant enclosure. The barrier system is designed to be assembled and set up in advance on the structure in preparation of a fire. Next L. A U.S. Pat. No. 9,381,387 by Douglas was issued in 2016 for a FIRE-PROTECTION MECHANISM. It is a fire-protection mechanism that includes multiple, overlapping cavities that can be filled with water (and, more generally, a fluid). When the fire-protection mechanism is deployed over an object, such as a building, and the cavities are filled with water, the fire-protection mechanism reduces the likelihood that the object is damaged by the heat associated with a fire proximate to the object, such as a wild fire. In particular, the heat capacity and latent heat of the water significantly increase the thermal time constant of the object, thereby reducing the likelihood of combustion.

M. A US Patent Application Published as 2005/0022466A1 by Kish et al. in 2005 for a FIRE RESISTANCE RATING SYSTEM. It is a system for building structure fire resistance that can be rated by providing a new or existing building structure; providing or having made available at least one fire control agent; applying or noting application or presence of the at least one fire control agent to or with at least one component part of the building structure; providing a rating format for fire resistance of a comparative building structure; and comparing the applying, application or presence of or with the at least one component part of the building structure to the rating format to provide a fire resistance classification rating. A multi-level rating system can be employed. N. A US Patent Application Published as 2005/0170725A1 by Kimener in 2005 for a WILDFIRE PROTECTION. It shows and teaches a method of protecting an asset from destruction resulting from exposure to at least one of fire and thermal energy comprising: (a) identifying a pending threat capable of at least substantially destroying an asset by exposure to at least one of fire and thermal energy; (b) deploying a barrier, that includes a fire resistant layer and a thermal energy reflective layer, to separate the asset from the pending threat; and (c) securing the barrier to at least one of the ground, the asset itself, and a support structure; (d) wherein the act of securing the barrier is operative to retain at least one of the fire resistant layer and the thermal energy shield layer between the asset and the pending threat. O. A US Patent Application Published as 2009/0301001A1 by Kish et al. in 2009 is for a FIRE RESISTANCE RATING SYSTEM. It shows that fire resistance can be rated for building structure by providing or having made available, and applying or noting application or presence of fire control agent(s) to or with component part(s) of the structure; providing a fire resistance rating format of a comparative structure; and comparing for a fire resistance classification rating (FRCR). P. A US Patent Application Published as 2010/0269449A1 by Bush et al. in for a FIRE RESISTANT STRUCTURES, FIRE RESISTANT INSULATIONS, AND A METHOD FOR FIRE PROTECTION. It is a fire-resistant structures, fire-resistant insulations, and a method for fire-proofing and fire-protection of permanent or temporary structures or objects. It measures fire-resistance for insulation and the method for fire-protection that comprises steps of providing a fire-protection for structures and objects subjected to fires, brush-fires or fire storms.

Q. A US Patent Application Published as 2012/0227990A1 by Burnham in 2012 for a TRACTABLE, FIRE-RESISTANT, THERMA-INSULATED COVERS AND ENCLOSURES. It deals with a set of protective covers made with fire-resistant and thermo-insulated blankets to shield diverse structures and objects from fire; inter-connective tent units forming protective surface passageways for sheltering and evacuating firemen at fire locations and for providing tactical shelter for security personnel; novel tent configurations having optimal packaging and surface coverage characteristics; and, ground-covering blankets for stopping ground-level fire and for diverse fire-fighting tactical applications. R. A US Patent Application Published as 2013/0048317A1 by Charlton in for a FIRE RETARDANT DELIVERY METHOD AND APPARATUS. A method and apparatus for delivering fire retardant to a ground fire from an aircraft. The apparatus includes a dispenser casing that dispenses fire retardant after the casing has been released from an aircraft. The apparatus includes a dispenser fuse that actuates the dispenser casing to dispense the fire retardant in response to one or more predetermined conditions. S. A US Patent Application Published as 2015/0083443A1 by Thompson in for a METHOD OF PROTECTING A STRUCTURE FROM A FIRE. A method of protecting a structure from a fire. The method comprises covering the structure with a fire-retardant liquid absorbent material and spraying fire-retardant liquid on the fire-retardant liquid absorbent material. In a second embodiment, there is a method wherein the fire-retardant liquid absorbent material is draped over with a high temperature insulation material in segments forming seams, after the fire-retardant liquid absorbent material is sprayed. A third method comprises layering a structure with a high temperature insulation material and then layering said high temperature insulation layer with a liquid absorbing layer. T. A US Patent Application Published as 2016/0047120A1 by Davis et al. in 2016 for a FIREPROOF HOME AND A FIRE PROOF HEAT BARRIER SHIELD STRUCTURE. This provides a fireproof barrier shield comprising the panels combined together to form a fireproof blanket placed on the building structure to protect the structure from flying embers, radiant heat and fire accidents. The panel comprises an inner heat retardant layer an outer heat reflective layer secured together using a heat resistant adhesive glue or thread. Each panel has several slots for receiving a fastener for combining the panels.

As can be observed, none of the prior art has anticipated or caused one skilled in the art of fire retardant and resistant devices and systems for protecting building systems to see this new invention by Paull as obvious to a person skilled in the ordinary art of the industry. The Special Fire Protection System for Runaway Grass and Forest Fires and Method for Use provides an answer to the need for protecting building structures with a fire resistant or retardant system. This protection of the building structure is provided by layering quickly the foam and retention system over the structures. The new invention prevents the fire from damaging the structure as well as providing an economic advantage of preserving the covered structure rather than replacing a destroyed structure.

SUMMARY OF THE INVENTION

This invention is a Special Fire Protection System for Runaway Grass and Forest Fires and Method for Use. The preferred embodiment of the Special Fire Protection System is a fire protection system for protecting residential, commercial and governmental structures from runaway grass and forest fires comprised of: (a) a heat reflective cover tarp, roll-out matting, or fold out matting with reflective surface on one or both sides, the tarp is configured to fully encase the structure; (b) a fire proof spray foam—approximately 2 to 12 inches, with fire retardant additive, normally closed cell and 800 to 1400 degree minimum resistivity, the foam is applied to fully encase the tarp; (c) multiple hold down straps, ropes, cable, etc.; (d) a prodding/push pole to tuck sprayed tarp into windows, door frames, soffits and under hangs; (e) a series of anchors—straight, augers, etc.; (f) a pre spray release coating (optional); and (g) a set of corner bands (optional) wherein the system, broadly considered, can be individually installed into a position to completely isolate a free standing structure from an external fire. The heat reflective tarp may be manufactured in standard sizes that can be readily customized to fit varying size structures. The fire resistant foam can be quickly installed over the tarp in depths of approximately 2 to 12 inches or more as desired if advantageous. When installed, this invention can prevent damage to a free standing structure and its contents from an external wild fire or firestorm.

OBJECTS AND ADVANTAGES

There are several objects and advantages of the Special Fire Protection System for Runaway Grass and Forest Fires and Method for Use. There are currently no known fire protective, fast deploying structural systems that are effective at providing the objects of this invention.

The Special Fire Protection System for Runaway Grass and Forest Fires and Method for Use has various advantages and benefits:

| Item | Advantages |
| --- | --- |
| 1 | Is fast to deploy onto structures; |
| 2 | Requires no water; |
| 3 | Can be used for residential, commercial and governmental structures - cover a wide variety of building structures; |
| 4 | Can be deployed in hot or wet environment; |
| 5 | Requires no pre-measurements; |
| 6 | Requires only simple training for installation and use; |
| 7 | Can pre deploy materials, if needed, in likely fire danger zones for a short time reactions to wildfires; |
| 8 | Can favorably impact insurance premiums; |
| 9 | Permits pre-planning and having materials staged near or at likely danger zones; |
| 10 | Provides a means for protecting valuable property and/or lives from approaching fires, notably rapidly-moving forest and brush fires, commonly referred to as "fire-storms"; |
| 11 | Provides a means to rapidly cover a man-made structure with a fire-resistant structure while maintaining a separate lining or an air space between the protected structure and the fire-resistant structure. |

Finally, other advantages and additional features of the present Special Fire Protection System for Runaway Grass and Forest Fires and Method for Use will be more apparent from the accompanying drawings and from the full description of the device. For one skilled in the art of fire protection systems for structures, it is readily understood that the features shown in the examples with this product are readily adapted to other types of fire and structural protection systems and methods.

DESCRIPTION OF THE DRAWINGS—FIGURES

The accompanying drawings, which are incorporated in and constitute a part of this specification, illustrate an embodiment of the Special Fire Protection System for Runaway Grass and Forest Fires and Method for Use that is preferred. The drawings together with the summary description given above and a detailed description given below serve to explain the principles of the System and Method. It is understood, however, that the Special Fire Protection System for Runaway Grass and Forest Fires and Method for Use is not limited to only the precise arrangements and instrumentalities shown.

FIGS. 1A through 1D are sketches of the special protection method and system for protecting structures from runaway grass and forest fires.

FIGS. 2A and 2B are sketches of the general prototype structure coating and fire source for initial testing of the protection system.

FIG. 4A is a sketch of the initial design sketch for the protection system for structures in runaway grass and food forest fires and FIG. 4B are typical ground anchors.

FIGS. 7A through 7E are sketches of the protection system for a modern west coast structure.

FIG. 8 is a listing of the process to deploy protection system onto structures for protection from runaway grass and forest fires.

FIGS. 9A and 9B are sketches of prior art for fire protection systems.

FIGS. 10A through 10C are more sketches of prior art fire protection systems.

FIGS. 11A through 11C are even more sketches prior art fire protection systems.

DESCRIPTION OF THE DRAWINGS—REFERENCE NUMERALS

Figure 3B:
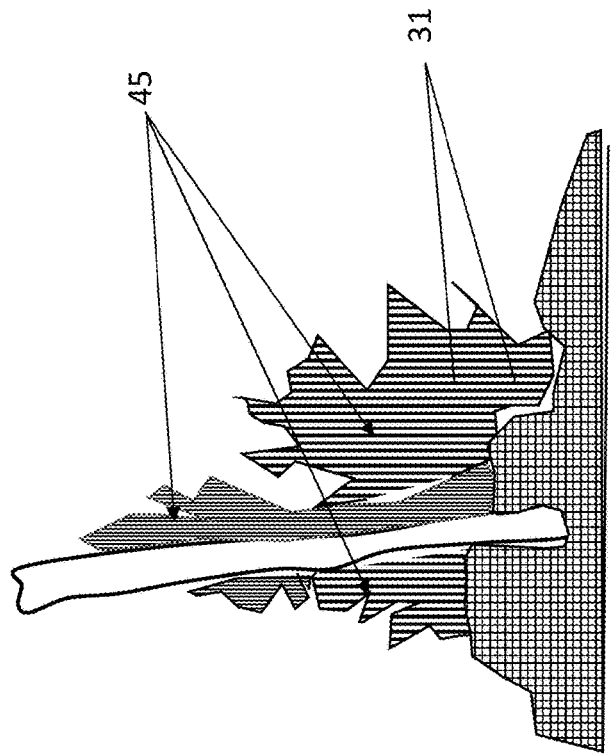
FIGS. 3A through 3C are sketches of the fire testing of prototype protection system with the components and features shown.

The following list refers to the drawings:

TABLE B

| Reference numbers | |
| --- | --- |
| Ref # | Description |
| 30 | Fire protection system 30 for protecting structures from runaway grass and forest fires |
| 31 | Prototype 31 of fire protection system 30 |
| 33 | Initial system design 33 for fire protection system 30 |
| 40 | Fire source 40 for testing prototype 31 |
| 45 | Resultant fire 45 for testing prototype 31 |
| 48 | Temperature read out 48 inside prototype 31 during test |
| 50 | Residential house structure 50 |
| 51 | Commercial building 51 strip mall, etc. |
| 52 | Modern residential 52 out West |
| 54 | Corner bands 54 (optional) |
| 55 | Pre spray release coating 55 |
| 56 | Heat reflective cover 56 tarp, roll/out matting, fold out matting with reflective surface on one or both sides |
| 57 | Fire proof spray foam 57 - approximately 2 to 12 inches, with fire retardant additive, normally closed cell and 800 to 1400 degree minimum resistivity; |
| 58 | Hold down straps 58, ropes, cable, etc. |
| 59 | Anchors 59 - straight legged, augers, angle legged, etc. |
| 59A | Prodding/push pole 59A to tuck sprayed tarp into windows, door frames, soffits and under hangs |
| 60 | Method 60 to protect structures from runaway grassed forest fires |
| 101 | Prior art 101 Pat. No. 5,423,150 drop cloth |
| 102 | Prior art 102 Pat. No. 4,858,394 cover and zip cloth |
| 103 | Prior art 103 Pat. No. 5,608,992 tent pole cover |
| 104 | Prior art 104 Pat. No. 5,860,251 water filled |
| 105 | Prior art 105 Publication No 2005/0170725 cable down |
| 106 | Prior art 106 Pat. No. 3,715,843 tarp strap cover |
| 107 | Prior art 107 Pat. No. 7,395,869 magnet cover |
| 108 | Prior art 108 Pat. No. 9,381,387 water cascade |

TABLE B-continued

Reference numbers

| Ref # | Description |
| --- | --- |
| 109 | Prior art 109 Publication No 2009/0269449 hut cover |
| 110 | Prior art 110 Publication No 2012/0227990 metro slide |

DETAILED DESCRIPTION OF PREFERRED EMBODIMENT

This invention relates to a Special Fire Protection System for Runaway Grass and Forest Fires and Method for Use. Simply stated it is related to fire protection systems for structures. The embodiments herein are particularly related to fire protection devices and accessories used for protecting building structures. The embodiments herein are more particularly related to fire protection sheet and insulating blanket of foam used for protecting building structures without direct physical attachments to the building structure. More particularly, the present invention relates to a design for fire-resistant structure deployed over buildings and other objects when confronted with an approaching fire. Furthermore, the present disclosure relates to system and method of use for a system that protect objects from damage or combustion when exposed to fire. This is a design of a system for emergency deployment in the event of the approach of hazardous conditions, especially rapidly moving fires commonly referred to as "fire storms." The present invention relates generally to a fire isolation covering system for free standing structures. More particularly, the present invention relates to a system for a fire resistant house cover which can be employed as well for other structures, residential and commercial.

The advantages for the Special Fire Protection System 30 for Runaway Grass and Forest Fires and Method for Use are listed above in the introduction. Succinctly the benefits are that the device:
A. Is fast to deploy onto structures;
B. Requires no water;
C. Can be used for residential, commercial and governmental structures—cover a wide variety of building structures;
D. Can be deployed in hot or wet environment;
E. Requires no pre-measurements;
F. Requires only simple training for installation and use;
G. Can pre deploy materials, if needed, in likely fire danger zones for a short time reactions to wildfires;
H. Can favorably impact insurance premiums;
I. Permits pre-planning and having materials staged near or at likely danger zones;
J. Provides a means for protecting valuable property and/or lives from approaching fires, notably rapidly-moving forest and brush fires, commonly referred to as "fire-storms"; and
K. Provides a means to rapidly cover a man-made structure with a fire-resistant structure while maintaining a separate lining or an air space between the protected structure and the fire-resistant structure.

The preferred embodiment of the Special Fire Protection System 30 is a fire protection system 30 for protecting residential, commercial and governmental structures from runaway grass and forest fires comprised of: (a) a heat reflective cover 56 tarp, roll-out matting, or fold out matting with reflective surface on one or both sides, the tarp is configured to fully encase the structure; (b) a fire proof spray foam 57—approximately 2 to 12 inches, with fire retardant additive, normally closed cell and 800 to 1400 degree minimum resistivity, the foam is applied to fully encase the tarp; (c) multiple hold down straps 58, ropes, cable, etc.; (d) a Prodding/push pole 59A to tuck sprayed tarp into windows, door frames, soffits and under hangs; (e) a series of anchors 59—straight, augers, etc.; (f) a pre spray release coating 55 (optional); and (g) a set of corner bands 54 (optional) wherein the system, broadly considered, can be individually installed into a position to completely isolate a free standing structure from an external fire. The heat reflective tarp may be manufactured in standard sizes that can be readily customized to fit varying size structures. The fire resistant foam can be quickly installed over the tarp in depths of approximately 2 to 12 inches or more as desired if advantageous. When installed, this invention can prevent damage to a free standing structure and its contents from an external wild fire or firestorm.

There is shown in FIGS. 1-12 a complete description and operative embodiment of the Special Fire Protection System 30 for Runaway Grass and Forest Fires and Method for Use. In the drawings and illustrations, one notes well that the FIGS. 1-12 demonstrate the general configuration and use of this product. The various example uses are in the operation and use section, below.

The accompanying drawings, which are incorporated in and constitute a part of this specification, illustrate a preferred embodiment of the Special Fire Protection System 30 for Runaway Grass and Forest Fires. The drawings together with the summary description given above and a detailed description given below serve to explain the principles of the Special System 30 and the method is described in the section below. It is understood, however, that the special system 30 is not limited to only the precise arrangements and instrumentalities shown. Other examples of fire protection systems and uses are still understood by one skilled in the art of fire protection systems to be within the scope and spirit shown here.

FIGS. 1A through 1D are sketches of the special protection method and system for protecting structures from runaway grass and forest fires. Shown here are a set of sketches summarizing the invention presented here. Included are: a fire protection system 30 for protecting structures from runaway grass and forest fires; a prototype 31 of fire protection system 30; and the method 60 to protect structures from runaway grassed forest fires.

FIGS. 2A and 2B are sketches of the general prototype structure 31 coating and fire source 40 for initial testing of the protection system. This is in preparation for the test to demonstrate the effectiveness of the heat reflective tarp coupled with the foam with fire retardant additive place approximately 2 to 12 inches thick over the entire structure.

Figure 3A:
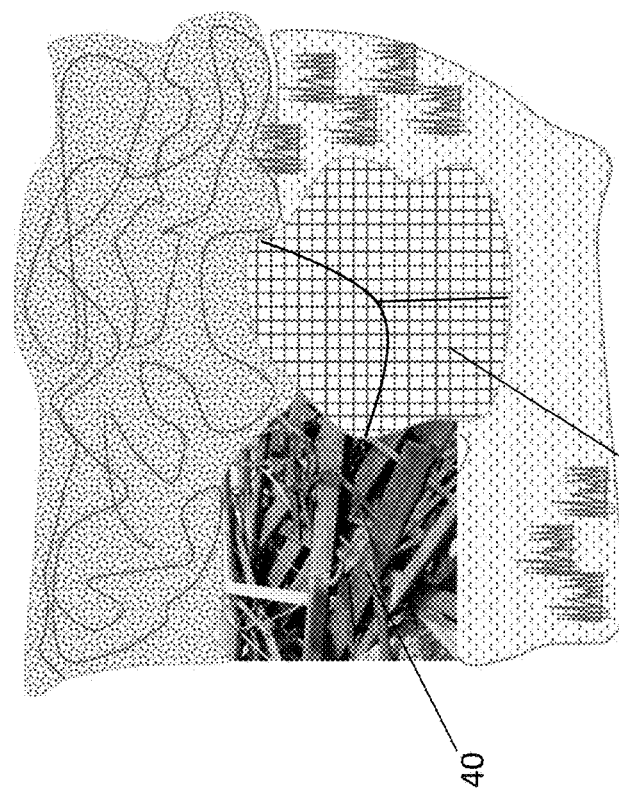
Figure 3C:
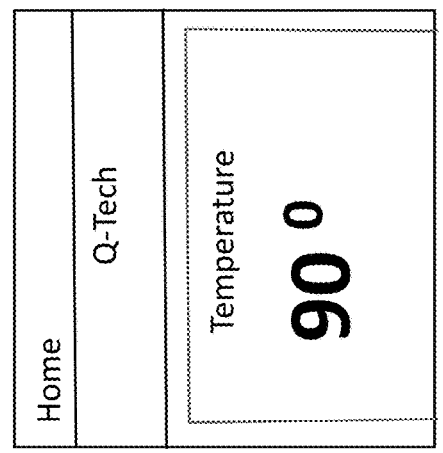
Figure 5A:
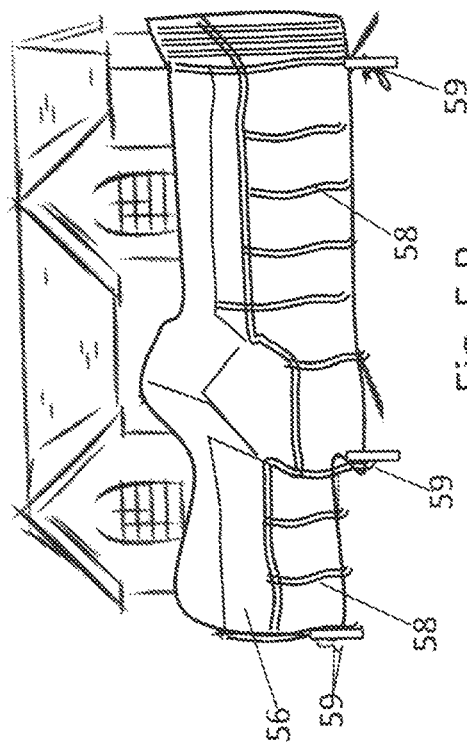
FIGS. 5A through 5D are sketches of the protection system with a two story residential structure.
Figure 5B:
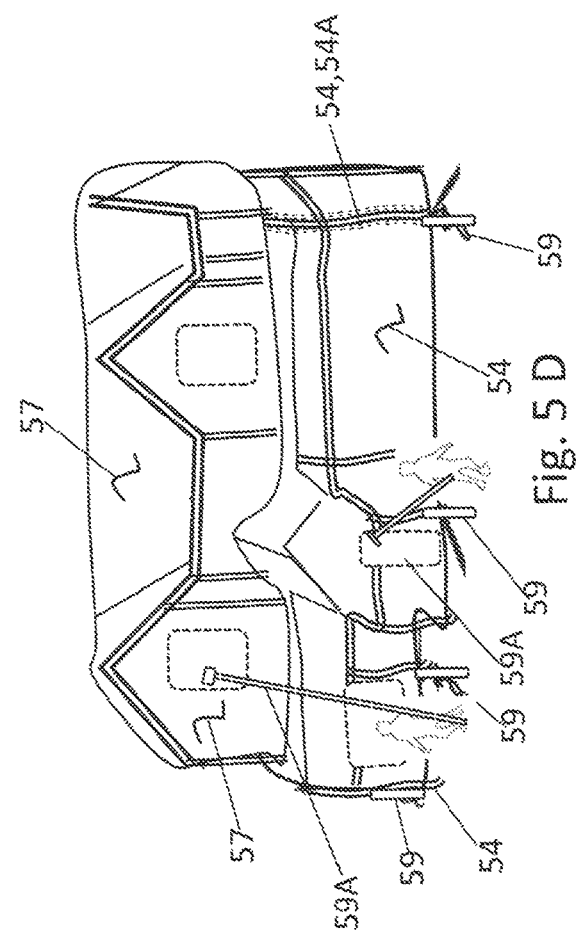
Figure 5C:
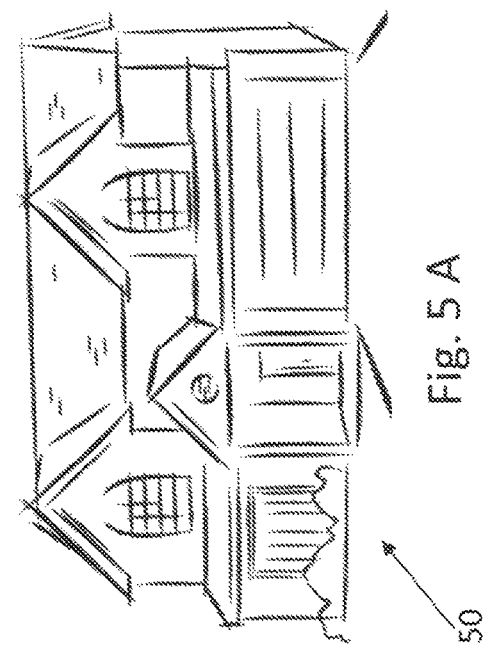
Figure 5D:
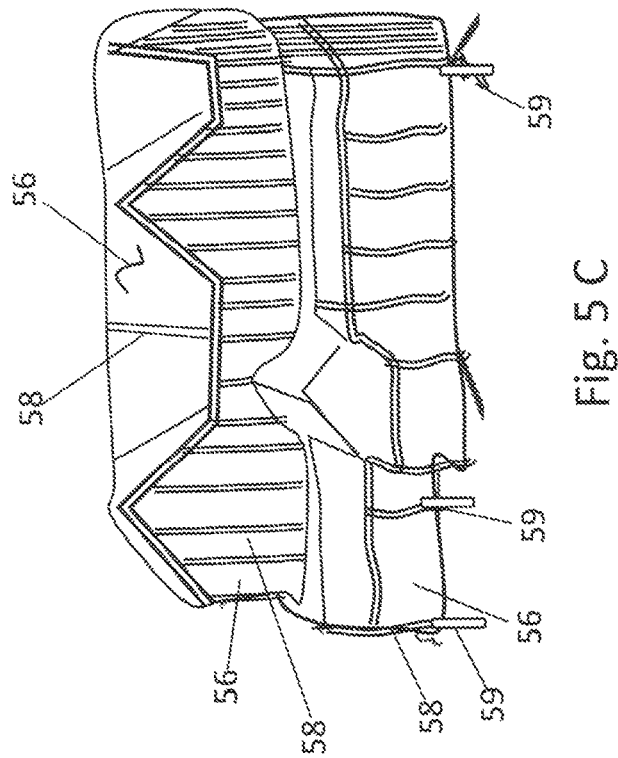
Figure 6A:
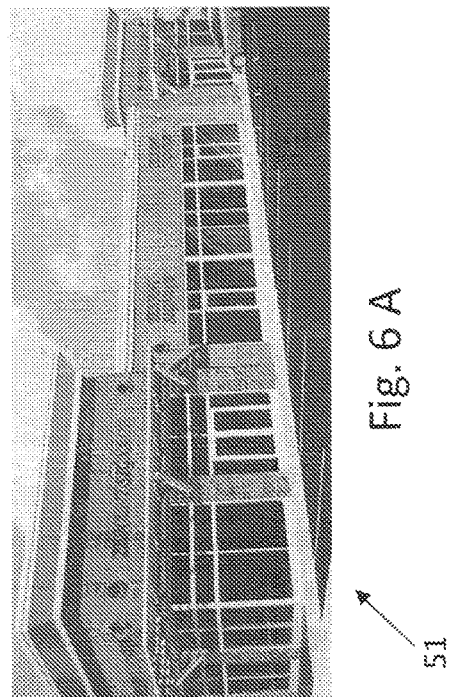
FIGS. 6A through 6D are sketches of the protection system for a small strip mall structure.
Figure 6B:
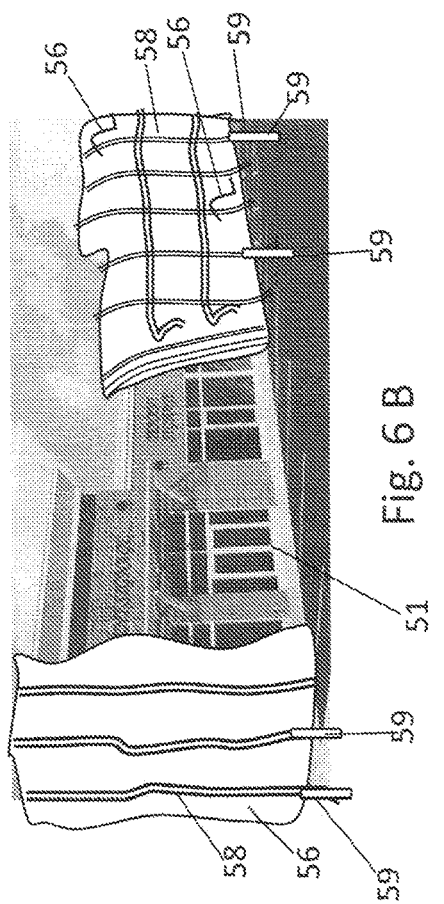
Figure 6C:
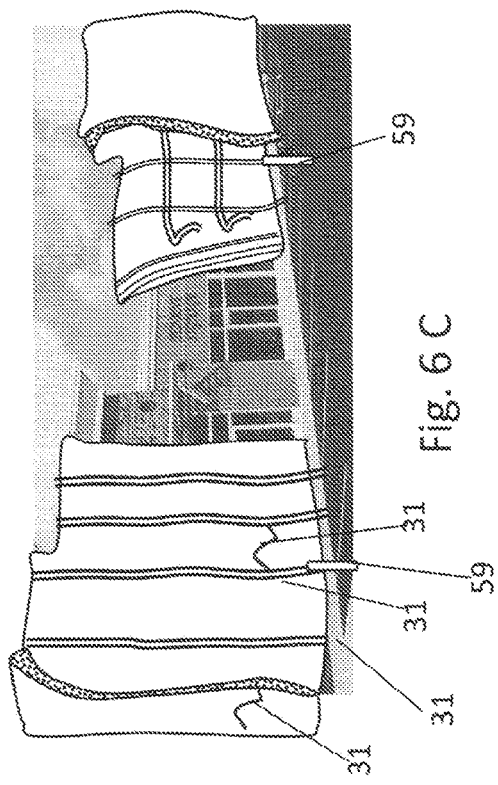
Figure 6D:
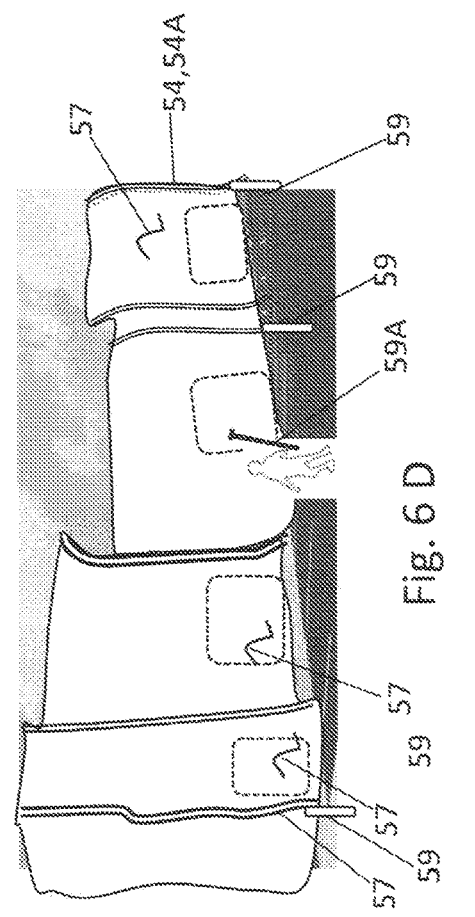
Figure 12:
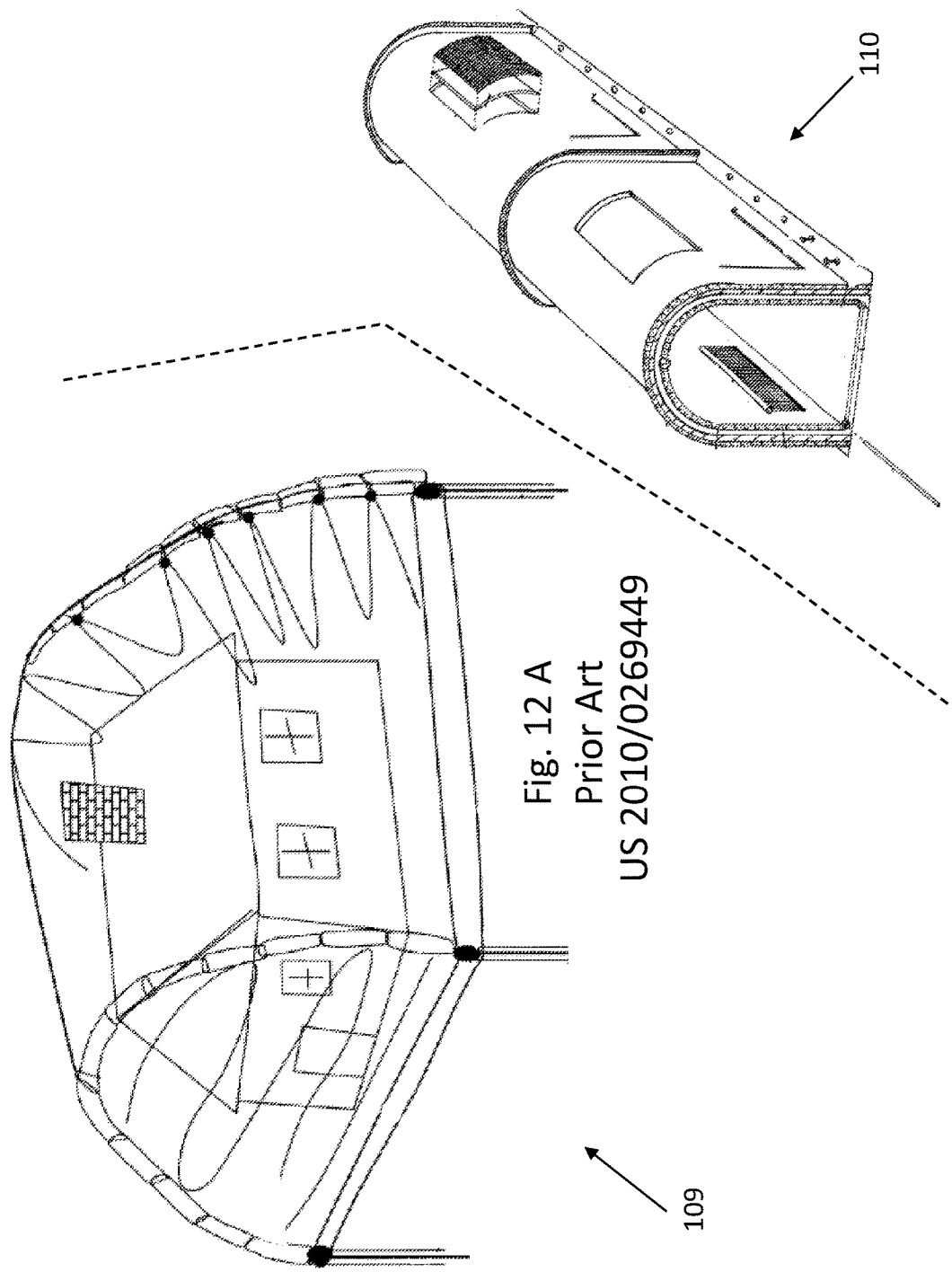
FIGS. 12A and 12B are more fire protection systems from prior art.

FIGS. 3A through 3C are sketches of the fire testing of prototype 31 protection system with the components and features shown. In these views are seen: a prototype 31 of fire protection system 30; a fire source 40 for testing prototype 31; the resultant fire 45 for testing prototype 31; and a temperature read out 48 inside prototype 31 during test. The test results show an internal test temperature of 90 degrees when exposed to the raging inferno outside the structure protected by the protective a fire protection system 30 for protecting structures from runaway grass and forest fires. This was a successful test for the system and proved a good method to install the tarp and foam onto the structures.

FIG. 4A is a sketch of the initial design sketch 33 for the protection system for structures in runaway grass and food forest fires and FIG. 4B are typical ground anchors 59. Here are shown: the initial system design 33 for fire protection system 30 and a series of various types of anchors 59—straight leg, augers, angled legged, etc. A pre-spray release coating 55 (optional) was added later if any (unforeseen and unexpected) problems are encountered with releasing the tarp from the structure.

FIGS. 5A through 5D are sketches of the protection system 30 with a two story residential structure. In these views, the structure 50 is seen, them the tarps, straps and anchors, and finally the foam. In a complete description is viewed: a fire protection system 30 for protecting structures from runaway grass and forest fires; a residential house structure 50; a set of corner bands 54 (optional); wide seal tape 54A cover corners 54; a pre spray release coating 55 (optional); a heat reflective cover 56 tarp, roll-out matting, fold-out matting with reflective surface on one or both sides; a fire proof spray foam 57—approximately 2 to 12 inches, with fire retardant additive, normally closed cell and 800 to degree minimum resistivity; multiple hold down straps 58 straps, ropes, cable, etc.; prodding/push pole 59A to tuck sprayed tarp into windows, door frames, soffits and under hangs; and series of anchors 59—straight, augers, etc.

FIGS. 6A through 6D are sketches of the protection system for a small strip mall structure 51. Here are viewed, similarly to the house structure 50, a fire protection system 30 for protecting structures from runaway grass and forest fires; a small strip mall structure 51; a set of corner bands 54 (optional); wide seal tape 54A cover corners 54; a pre spray release coating 55 (optional); a heat reflective cover 56 tarp, roll-out matting, fold-out matting with reflective surface on one or both sides; a fire proof spray foam 57 —approximately 2 to 12 inches, with fire retardant additive, normally closed cell and 800 to 1400 degree minimum resistivity; multiple hold down straps 58 straps, ropes, cable, etc.; prodding/push pole 59A to tuck sprayed tarp into windows, door frames, soffits and under hangs; and series of anchors 59—straight, augers, etc.

FIGS. 7A through 7E are other sketches of the protection system for a modern west coast structure 52. Again, these sketches show: a fire protection system 30 for protecting structures from runaway grass and forest fires; a modern west coast structure 52; a set of corner bands 54 (optional); wide seal tape 54A cover corners 54; a pre spray release coating 55 (optional); a heat reflective cover 56 tarp, roll-out matting, fold-out matting with reflective surface on one or both sides; a fire proof spray foam 57 —approximately 2 to 12 inches, with fire retardant additive, normally closed cell and 800 to 1400 degree minimum resistivity; multiple hold down straps 58 straps, ropes, cable, etc.; prodding/push pole 59A to tuck sprayed tarp into windows, door frames, soffits and under hangs; and series of anchors 59—straight, augers, etc.

When connecting the heat reflective cover 56 tarp, roll-out matting, foldout matting with reflective surface on one or both sides, the pieces can be rapidly fabricated by well-known methods, usually involving a combination of sewing, gluing, heat sealing, welding, taping or otherwise attaching a multiplicity of pre-cut shapes of the fire-resistant tarp/fabric 56 to form the desired shape upon deployment.

FIG. 8 is a listing of the method to process 60 and deploy the protection system 60 onto structures for protection from runaway grass and forest fires. This is described in the operation section below.

FIGS. 9A and 9B are sketches of prior art for fire protection systems. Here former patents and applications of fire protection system, including: Prior art 101 U.S. Pat. No. 5,423,150—a large drop cloth covering and Prior art 102 U.S. Pat. No. 4,858,394—a cover and zip/closure device.

FIGS. 10A through 10C are more sketches of prior art fire protection systems. Here former patents and applications of fire protection system, including: Prior art 103 U.S. Pat. No. 5,608,992—classic tent poles with a cover device; Prior art 104 U.S. Pat. No. 5,860,251—a water filled cover; and Prior art 105 Publication No 2005/0170725—a cover with a cable hold-down.

FIGS. 11A through 11C are even more sketches prior art fire protection systems. Here former patents and applications of fire protection system, including: Prior art U.S. Pat. No. 3,715,843—a basic tarp and strap covering device; Prior art 107 U.S. Pat. No. 7,395,869—a cover with a magnetic holding means; and Prior art 108 U.S. Pat. No. 9,381,387—a water cascade covering structure.

FIGS. 12A through 12B are more fire protection systems from prior art. Here former patents and applications of fire protection system, including: Prior art 109 Publication No 2010/0269449—a hut covering; Prior art 110 Publication No 2012/0227990—a metro slide covering As can be seen, the Special Fire Protection System for Runaway Grass and Forest Fires and Method for Use is a unique combination and use as described herein. Above are seen numerous innovations for fire isolation devices have been provided in the prior art that are adapted to be used. Even though these innovations may be suitable for the specific individual purposes to which they address, they would not be suitable for the purposes of the present invention as heretofore described.

The details mentioned here are exemplary and not limiting. Other specific components and manners specific to describing a Special Fire Protection System 30 for Runaway Grass and Forest Fires and Method for Use can be added as a person having ordinary skill in the field of the art of fire protection systems and methods for their uses well appreciates.

OPERATION OF THE PREFERRED EMBODIMENT

The Special Fire Protection System 30 for Runaway Grass and Forest Fires and Method for Use has been described in the above embodiment. The manner of how the device operates is described below. One notes well that the description above and the operation described here must be taken together to fully illustrate the concept of Special Fire Protection System for Runaway Grass and Forest Fires and Method for Use. The preferred embodiment of the Special Fire Protection System for Runaway Grass and Forest Fires was described above. The method of use is described here.

FIG. 8 is a listing of the process 60 to deploy protection system 30 onto structures for protection from runaway grass and forest fires. The Method is:

| Step | Description |
| --- | --- |
| 1 | Spray structure with release agent (optional) |
| 2 | Cover structure with heat reflective layer (tarp or roll matting/layered material) |
| 3 | Cover corners with wide seal tape if needed |
| 4 | Secure reflective layer with straps |
| 5 | Attach ground straps to ground anchors |
| 6 | Spray-on approximately 2 to 12 inches fire protective foam |
| 7 | Prod/press pole into window frames, soffits, under-hangs etc. as foam cures and sets-up |

| Step | Description |
| --- | --- |
| 8 | Spray on alternative intumescent coating/foam |
| 9 | Roll-on Alternative Heat retardant coating |
| 10 | Post fire - remove foam |
| 11 | Unsecure ground straps from anchors |
| 12 | Remove anchors |
| 13 | Remove reflective heat cover/tarp/layer |
| 14 | Pressure spray surface to remove residue if needed |

Many uses are anticipated for the Special Fire Protection System 30 for Runaway Grass and Forest Fires and Method for Use. Some examples, and not limitations, are shown in the following Table.

| ITEM | DESCRIPTION |
| --- | --- |
| 1 | multi-level residential |
| 2 | single level residential |
| 3 | commercial buildings |
| 4 | schools and government buildings |
| 5 | barns and ranch outbuildings |
| 6 | strip malls |
| 7 | convenience stores |
| 8 | power transmission line towers |
| 9 | cellular telephone towers |
| 10 | statues, gazebos, pool houses |
| 11 | garages, stables, and workshops |
| 12 | barns, outbuildings |

With this description it is to be understood that the Special Fire Protection System 30 for Runaway Grass and Forest Fires and Method for Use 60 is not to be limited to only the disclosed embodiment of product. The features of the Special System 30 are intended to cover various modifications and equivalent arrangements included within the spirit and scope of the description.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present inventions, the preferred methods and materials are now described above in the foregoing paragraphs.

Other embodiments of the invention are possible. Although the description above contains much specificity, these should not be construed as limiting the scope of the invention, but as merely providing illustrations of some of the presently preferred embodiments of this invention. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The terms recited in the claims should be given their ordinary and customary meaning as determined by reference to relevant entries (e.g., definition of "plane" as a carpenter's tool would not be relevant to the use of the term "plane" when used to refer to an airplane, etc.) in dictionaries (e.g., widely used general reference dictionaries and/or relevant technical dictionaries), commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used herein in a manner more expansive than its ordinary and customary meaning, the term should be given its ordinary and customary meaning plus the additional expansive meaning, or (b) if a term has been explicitly defined to have a different meaning by reciting the term followed by the phrase "as used herein shall mean" or similar language (e.g., "herein this term means," "as defined herein," "for the purposes of this disclosure [the term] shall mean," etc.). References to specific examples, use of "i.e.," use of the word "invention," etc., are not meant to invoke exception (b) or otherwise restrict the scope of the recited claim terms. Other than situations where exception (b) applies, nothing contained herein should be considered a disclaimer or disavowal of claim scope. Accordingly, the subject matter recited in the claims is not coextensive with and should not be interpreted to be coextensive with any particular embodiment, feature, or combination of features shown herein. This is true even if only a single embodiment of the particular feature or combination of features is illustrated and described herein. Thus, the appended claims should be read to be given their broadest interpretation in view of the prior art and the ordinary meaning of the claim terms.

Unless otherwise indicated, all numbers or expressions, such as those expressing dimensions, physical characteristics, etc. used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

The present invention contemplates modifications as would occur to those skilled in the art. While the disclosure has been illustrated and described in detail in the figures and the foregoing description, the same is to be considered as illustrative and not restrictive in character, it being understood that only selected embodiments have been shown and described and that all changes, modifications and equivalents that come within the spirit of the disclosures described heretofore and or/defined by the following claims are desired to be protected.

What is claimed is:

1. A fire protection system for protecting a free-standing structure that is a residential structure, a commercial structure, or a governmental structure from runaway grass and forest fires, wherein the system can be fabricated and later removed after a fire, and comprises:
(a) a heat reflective cover with two side surfaces, wherein at least one of the side surfaces of the heat reflective cover is a reflective surface and the heat reflective cover is configured to fully encase an exterior of the free-standing structure;
(b) at least one hold down strap placed vertically to a ground surface and externally to the heat reflective cover and at least one hold down strap placed horizontally to the ground surface, placed encircling the free-standing structure, and placed externally to the heat reflective cover;
(c) a series of anchors placed into the ground surface, and each anchor of the series of anchors attached to an end of a hold down strap of the at least one hold down strap placed vertically;
(d) a fire-proof spray foam layered between 1.9 inches and 12.1 inches in thickness and with a minimum heat resistivity between 800 degrees Celsius and 1400 degrees Celsius, the fire-proof spray foam fully encasing the heat reflective cover, the at least one hold down strap placed vertically, the at least one hold down strap placed horizontally, the anchors, a set of corner bands, and a seal tape; and
(e) a prodding/push pole to tuck the fire-proof spray foam and the heat reflective cover into a window, a door frame, a soffit, and an under-hang of the free-standing structure;
wherein the system can be individually installed into a position to completely isolate the free-standing structure from an external fire; wherein the heat reflective cover can be manufactured in sizes that can be customized to fit the free-standing structure; and wherein when installed, the system can prevent damage to the free-standing structure and its contents from an external wild fire or firestorm.

2. The fire protection system in claim 1 wherein the two side surfaces of the heat reflective cover are both reflective surfaces.

3. The fire protection system in claim 1 further comprising a pre-spray release coating on an outer surface of the heat reflective cover.

4. The fire protection system in claim 1 further comprising a set of corner bands wherein each corner band of the set is placed at each external corner of the free-standing structure and is sealed with a seal tape.

5. The fire protection system in claim 1 wherein the fire-proof spray foam further comprises a fire-retardant additive.

6. The fire protection system in claim 1 wherein the fire-proof spray foam further comprises a configuration of normally closed cells.

7. The fire protection system in claim 1 wherein the heat reflective cover is selected from a group consisting of a tarp, a roll-out mat, and a fold-out mat.

8. The fire protection system in claim 1 wherein the series of anchors is selected from a group consisting of straight legged stakes, augers, and angle-legged stakes.

9. A fire protection system for protecting a free-standing structure that is a residential structure, a commercial structure, or a governmental structure from runaway grass and forest fires, wherein the system can be fabricated and later removed after a fire, and comprises:
(a) a heat reflective cover with two side surfaces, wherein at least one of the side surfaces of the heat reflective cover is a reflective surface and the heat reflective cover is configured to fully encase an exterior of the free-standing structure;
(b) at least one hold down strap placed vertically to a ground surface and externally to the heat reflective cover and at least one hold down strap placed horizontally to the ground surface and externally to the heat reflective cover;
(c) a series of anchors placed into the ground surface, each anchor of the series of anchors attached to an end of a hold down strap of the at least one hold down strap placed vertically;
(d) a pre-spray release coating;
(e) a set of corner bands wherein each corner band of the set is placed at each external corner of the free-standing structure and is sealed with a seal tape;
(f) a fire-proof spray foam layered between 1.9 inches and 12.1 inches in thickness and with a minimum heat resistivity between 800 degrees Celsius and 1400 degrees Celsius, the fire-proof spray foam fully encasing an exterior of the heat reflective cover, the at least one hold down strap placed vertically, the at least one hold down strap placed horizontally, the anchors, the set of corner bands, and the seal tape; and
(g) a prodding/push pole to tuck the fire-proof spray foam and the heat reflective cover into a window, a doorframe, a soffit, and an under-hang of the free-standing structure;
wherein the system can be individually installed into a position to completely isolate the free-standing structure from an external fire; wherein the heat reflective cover can be manufactured in sizes that can be customized to fit the free-standing structure; and wherein when installed, the system can prevent damage to the free-standing structure and its contents from an external wild fire or firestorm.

* * * * *